United States Patent [19]

Sadkhin

[11] Patent Number: 5,366,483
[45] Date of Patent: Nov. 22, 1994

[54] METHOD AND APPARATUS FOR USE IN TREATING BIOLOGICALLY ACTIVE POINTS ON A PATIENT'S SKIN

[76] Inventor: Grigory Sadkhin, 1776 West 13th St., Brooklyn, N.Y. 11223

[21] Appl. No.: 60,758

[22] Filed: May 12, 1993

[51] Int. Cl.$^5$ ............................................. A61N 1/00
[52] U.S. Cl. ....................................... 607/3; 128/736; 128/907; 607/96
[58] Field of Search ..................... 607/2, 3, 96, 98, 99, 607/108, 115; 606/201, 204, 27, 28, 29, 31, 32; 128/736, 734, 735, 905, 907

[56] References Cited

U.S. PATENT DOCUMENTS

| | | | |
|---|---|---|---|
| 4,014,323 | 3/1977 | Gilmer et al. | 128/905 |
| 4,232,682 | 11/1980 | Veth | 128/736 |
| 4,407,295 | 10/1983 | Steuer et al. | 128/736 |
| 4,763,657 | 8/1988 | Chan et al. | 607/96 |
| 4,819,656 | 4/1989 | Spector | 128/736 |
| 4,940,060 | 7/1990 | Gu et al. | 128/907 |
| 5,195,517 | 3/1993 | Chen | 607/3 |

FOREIGN PATENT DOCUMENTS 2236190  3/1991  United Kingdom .................. 600/22

*Primary Examiner*—William E. Kamm
*Assistant Examiner*—John P. Lacyk
*Attorney, Agent, or Firm*—R. Neil Sudol; Henry D. Coleman

[57] ABSTRACT

A method for use in treating a patient includes the steps of sensing temperature at a first predetermined point on the patient's skin, generating a first electrical signal encoding the sensed temperature, transmitting the first electrical signal to a computer, measuring electrical skin resistance at a second predetermined point on the patient's skin, generating a second electrical signal encoding the measured electrical skin resistance, and transmitting the second electrical signal to the computer. The computer is operated to automatically determine a mode, duration and intensity of treatment on at least one treatment point on the patient's skin in response to the first electrical signal and the second electrical signal. A treatment of the mode, duration and intensity determined by the computer is applied to the treatment point either through manual setting of controls or automatically under computer control.

37 Claims, 3 Drawing Sheets

METHOD AND APPARATUS FOR USE IN TREATING BIOLOGICALLY ACTIVE POINTS ON A PATIENT'S SKIN

BACKGROUND OF THE INVENTION

This invention relates to a method and an associated apparatus for use in treating biologically active points on a patient's skin.

It is well established in the fields of acupuncture, reflexology, and applied kinesiology that the body has so called biologically active points which can be treated, for example, with needles or with the application of pressure, to relieve tensions and normalize the functioning of internal organs and muscles. The locations of these treatment points, for example, on so called meridians, are well established and fixed.

The condition of a patient's internal organs and musculature can also be diagnosed to some extent by testing temperature and electrical skin resistance at the same biologically active points on the skin. Probes for sensing temperature and skin resistance are well known.

OBJECTS OF THE INVENTION

An object of the present invention is to provide a method for facilitating the treatment of so called biologically active points on a patient's skin.

Another object of the present invention is to provide an associated apparatus for facilitating the treatment of so called biologically active points on a patient's skin.

Another, more particular, object of the present invention is to provide such a method and/or apparatus which at least partially automates the treatment process by operating a computer to control one or more treatment parameters in response to instructions from a user or practitioner.

An even particular object of the present invention is to provide such a method and/or apparatus in which intensity and duration of treatment are controlled by computer.

Yet another specific object of the present invention is to provide a treatment probe which can apply a selectable number and kind of treatment modalities simultaneously to a treatment point on a patient's skin.

These and other objects of the present invention will be apparent from the drawings and detailed descriptions herein.

SUMMARY OF THE INVENTION

A method for use in treating a patient comprises, in accordance with the present invention, the steps of (a) measuring at least one predetermined physiological parameter at a predetermined point on the patient's skin, the parameter being taken from the group including temperature and electrical skin resistance, (b) generating an electrical signal encoding the measured physiological parameter, (c) transmitting the electrical signal to a computer, (d) operating the computer to automatically determine a range of normal values of the physiological parameter at the predetermined point, and (e) displaying the range and a value of the measured physiological parameter on a display.

Preferably, the measurement of skin temperature and resistance is effectuated via probes or sensors having replaceable operative tips. Accordingly, a 2 mm probe tip can be used for diagnostic points on the ear and can be replaced with a 3 mm probe tip for measurement of skin temperature or resistance at other points on a patient's body.

According to another feature of the present invention, the method further comprises the step, executed subsequently to displaying the range and the parameter value, of treating the predetermined point with at least one of a plurality of treatment modes including pressure treatment, heat treatment, and electrical treatment.

The treatment step may be implemented by providing a treatment probe having first componentry for applying heat to the predetermined point and second componentry for conducting electrical current to the predetermined point, manually placing the treatment probe at the predetermined point, and automatically operating the treatment probe to control intensity and duration of the mode of treatment at the predetermined point upon the placement of the treatment probe there. Preferably, the treatment probe can be operated to apply any selectable combination of three treatment modalities to a particular treatment point. For example, pressure, heat and electricity may be applied simultaneously. Or just two modalities such as pressure and electricity may be applied.

In addition, the treatment probe preferably has replaceable operative tips. Accordingly, a 2 mm probe tip can be used for points on the ear while a 3 mm probe tip is used for other points on a patient's body.

The treatment step may include the step of controlling intensity and duration of application of a selected treatment mode, the method further comprising the step of displaying parameter settings identifying the mode, intensity and duration of treatment.

According to another feature of the present invention, the method further comprises the step, executed subsequently to the step of displaying, of treating an additional point on the patient different from the predetermined point with at least one of the treatment modes including pressure treatment, heat treatment, and electrical treatment.

A method for use in treating a patient comprises, in accordance with another conceptualization of the present invention, the steps of (i) providing a treatment probe having a heating component for applying heat to a predetermined point on a patient's skin surface and an electrical component for conducting electrical current to the predetermined point, (ii) manually placing the treatment probe at the predetermined point, (iii) operating either the heating component or the electrical component or both to apply a preselected treatment to the predetermined point on the patient, and (iv) automatically operating the treatment probe to control intensity and duration of the preselected treatment.

In accordance with another feature of this conceptualization of the present invention, a computer connected to the treatment probe is instructed as to the intensity and duration of the preselected treatment prior to the operation of the heating component or the electrical component. The computer is operated to control intensity and duration of treatment.

In many cases, a controlled amount of pressure is applied to the predetermined point on the patient's skin, in addition to controlled amounts of heat and electrical current.

In accordance with a further feature of the present invention, parameter settings identifying the mode, intensity and duration of treatment are displayed, e.g., on a monitor.

A device for use in treating a patient comprises, in accordance with the present invention, a handle, an operative tip connected to the handle, a first treatment component operatively connected to the tip for applying a generally selectable amount of heat to a predetermined point on a patient's skin via the tip, and a second treatment component operatively connected to the tip for applying a selectable amount of electrical energy to the predetermined skin point via the tip.

The operative tip can have different diameters, depending on the location of the treatment point. Treatment points on the ear require an operative tip approximately 2 mm in diameter, while treatment points at other locations on the body are treated with an operative tip 3 mm in diameter. Preferably, the treatment device has exchangeable tips.

Pursuant to another feature of the present invention, the first treatment component includes a first selector for selecting an amount of heat to be applied to the predetermined point, a heat exchanger operatively connected to the instrument tip for elevating the temperature thereof to a magnitude in accordance with a selection made via the first selector, and a first control operatively connected to the first selector and to the heat exchanger for controlling the operation thereof in accordance with a selection made via the first selector. The second treatment component includes a second selector for selecting an amount of electrical energy to be applied to the predetermined point, an electrical current generator operatively connected to the operative tip of the device tip for conducting through the tip an amount of current determined in accordance with a selection made via the second selector, and a second control operatively connected to the second selector and to the current generator for controlling the operation thereof in accordance with a selection made via the second first selector.

According to another feature of the present invention, the first treatment component includes a rotary drive operatively connected to the instrument tip for rotating the tip relative to the handle. A selector may be operatively connected to the rotary drive for selecting a rate of rotation of the tip relative to the handle.

According to a further feature of the present invention, the first selector includes circuitry for selecting a duration of application of heat to the predetermined point, while the second selector includes circuitry for selecting a duration of application of electrical energy to the predetermined point.

The first control and the second control may comprise a computer or microprocessor operatively connected to the selectors, the heat exchanger and the current generator for controlling duration and intensity of heat application via the heat exchanger and duration and intensity of electrical energy application via the current generator in response to the operation of the selectors.

A video monitor is advantageously connected to the computer for displaying mode, duration and intensity of treatment.

According to yet another feature of the present invention, the device further comprises a third treatment component operatively connected to the instrument tip for automatically controlling the degree of pressure applied to the patient's skin via the tip.

The second treatment component preferably includes means for controlling voltage and frequency of an electrical signal applied to the patient's skin at the predetermined point.

A mechanical support is advantageously connected to the treatment probe for supporting the probe at the treatment point upon manually positioning of the probe at the treatment point.

It is to be noted that a treatment probe in accordance with the present invention can be operated to apply any selectable combination of three treatment modalities to any treatment point. Pressure, heat and electricity may be applied simultaneously. Alternatively, pressure and electricity may be applied, or heat and electricity. The modalities may also be applied singly.

A method and associated apparatus in accordance with the present invention facilitate the treatment of so called biologically active points on a patient's skin. The ranges of normal temperature and electrical resistance for each of a plethora of biologically active points on a patient's skin are made available instantly. In response to pretreatment settings made via the selectors by an operator, a computer automatically controls treatment parameters such as mode, intensity and duration of treatment. Accordingly, reproducibility of tests and treatments is enhanced.

A printer may be provided for printing out a record of the examination and treatment of each patient.

DETAILED DESCRIPTION

Figure 1:
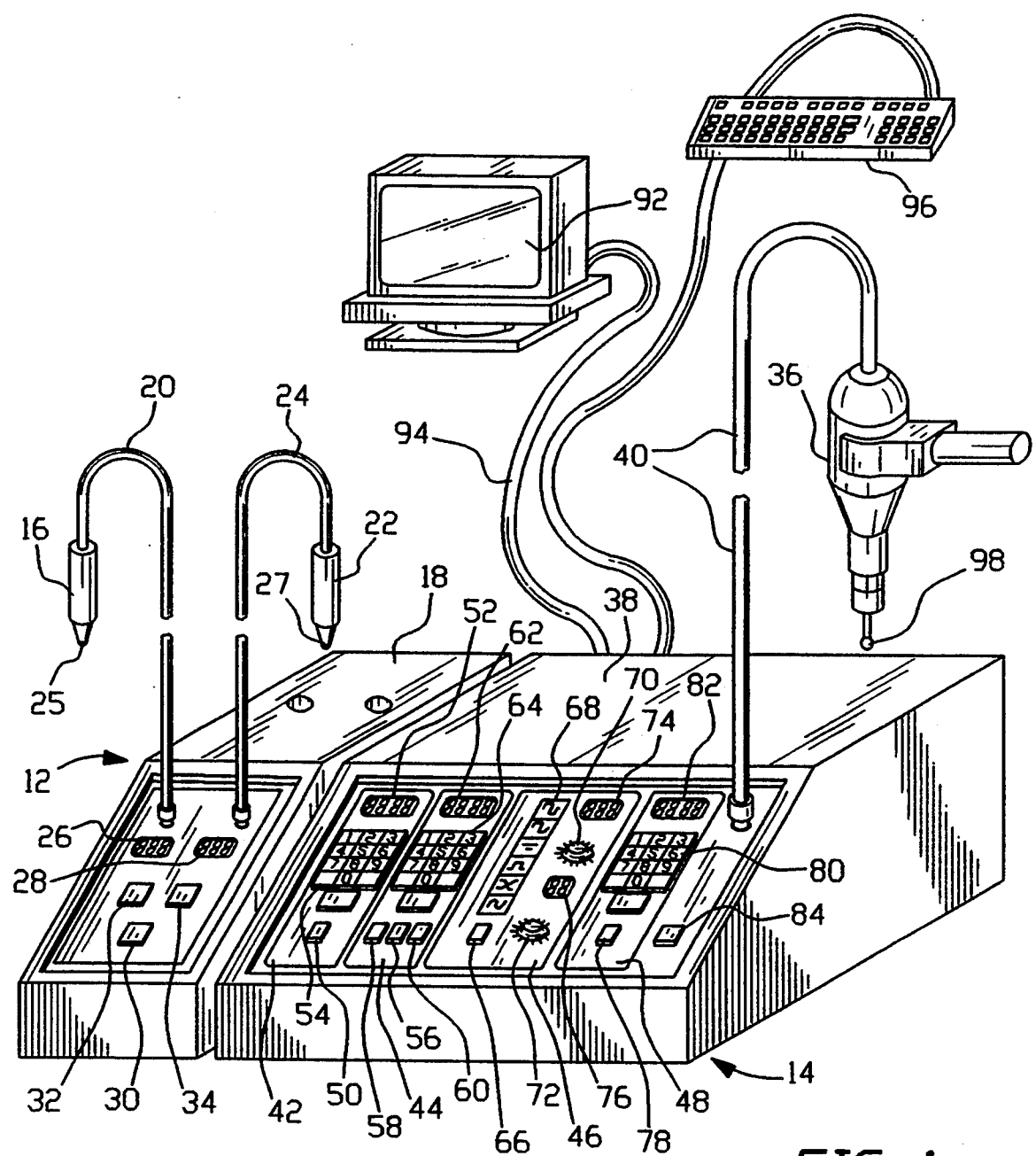
FIG. 1 is an isometric view of an apparatus in accordance with the present invention for diagnosing and treating biologically active points on a patient's skin.
Figure 2:
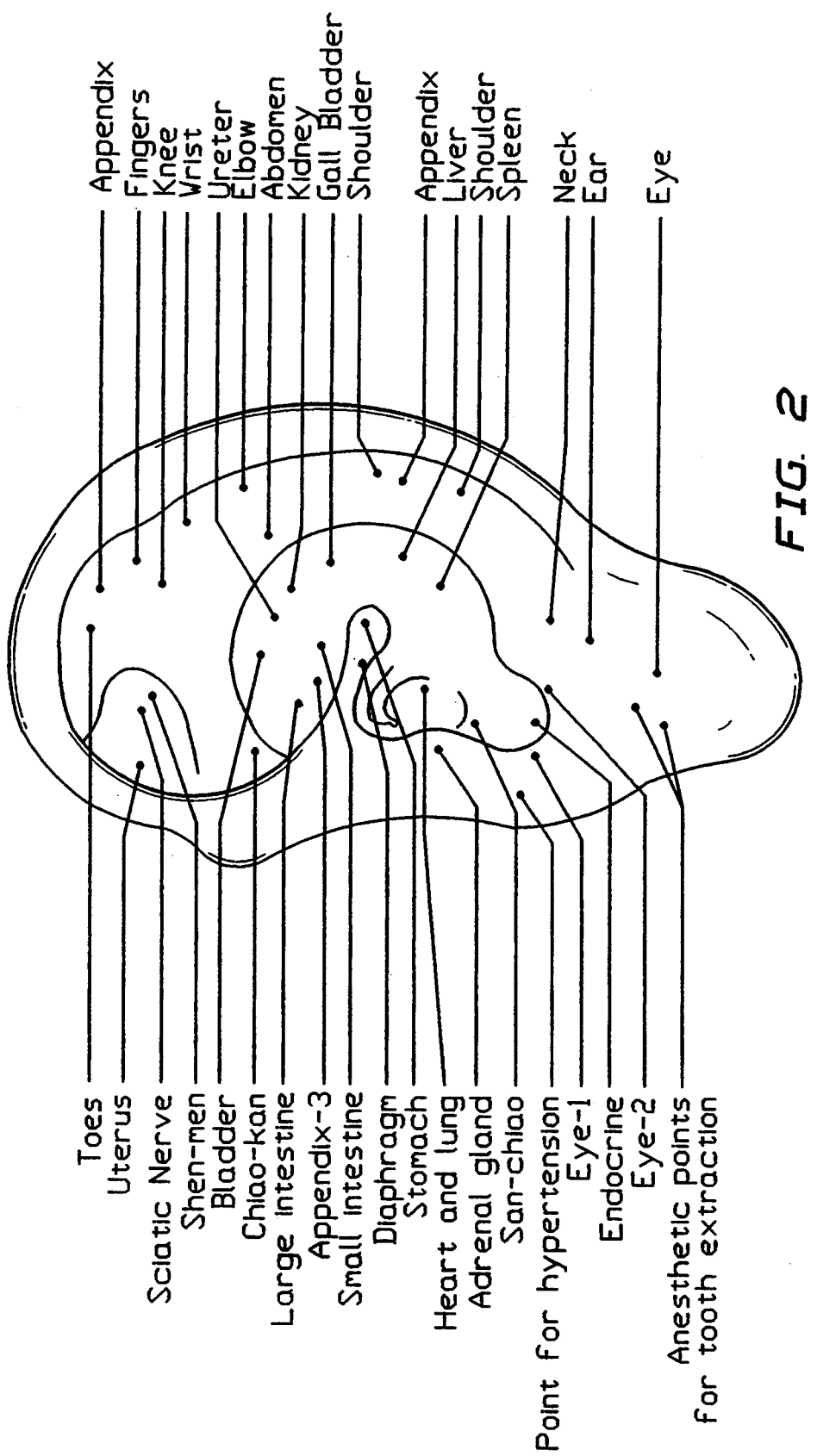
FIG. 2 is a diagram showing relative locations of biologically active points on the ear.

As illustrated in FIG. 1, an apparatus for use in diagnosing and treating biologically active points (e.g., acupressure points) on a patient's skin comprises a diagnostic and monitoring unit 12 and a functional or treatment unit 14. Diagnostic unit 12 includes a hand-held temperature sensing probe 16 connected to a housing 18 via a signal transmission line 20. Temperature probe 16 is used to sense the temperature at different diagnostic/treatment points on a patient's skin. FIG. 2 shows the locations of such points on the ear. These diagnostic and/or treatment points are well known in the healing arts of acupuncture, reflexology, applied kinesiology, etc. The biologically active points are conventionally treated, for example, with needles or with the application of pressure, to relieve tensions and normalize the functioning of internal organs and muscles.

Diagnostic unit 12 also includes a second hand-held probe 22 connected to housing 18 via another signal transmission line 24. Probe 22 is used to measure electrical skin resistance at diagnostic points such as those illustrated in FIG. 2. Diagnostic and treatment points are found at other locations over the body, for example, on the soles of the feet and on the nose.

Probes 16 and 22 are each provided with an operative or functional tip 25 and 27 approximately 2 mm in diameter which can be replaced by another tip (not shown) approximately 3 mm in diameter. The 2 mm tip 25 or 27 is for diagnosing temperature or electrical skin resistance at points on the ear (FIG. 2), while the 3 mm tip is used for diagnostic points at other locations on a patient's body.

Housing 18 is provided with digital displays 26 and 28 for displaying the temperature and skin resistance respectively measured by probes 16 and 22. A power switch 30 for diagnostic and monitoring unit 12 and activation buttons 32 and 34 for enabling the functioning of probes 16 and 22, respectively, are provided on housing 18.

Functional or treatment unit 14 includes a hand-held treatment device or press therapy probe 36 operatively connected to a housing 38 via a signal transmission line 40. Treatment probe 36 is used to apply controlled amounts of pressure, heat and/or electrical current to selected treatment points on a patient. To that end, housing 38 has indicator and control panels 42, 44, and 46 for acupressure, thermopuncture and electro-acupuncture, respectively. Another panel 48 is provided for timing indication and control.

Panel 42 includes an on/off switch 50, a digital display 52 for indicating the applied pressure, and a keypad 54 for selecting a desired pressure to be applied via treatment probe 36. Panel 44 includes an on/off switch 56, buttons 58 and 60 for selecting the direction of rotation of a rotating tip of probe 36, a digital display 62 for indicating the actual instantaneous rotational speed of the tip of treatment probe 36, and a keypad 64 for selecting a desired rotational speed of the probe tip. Panel 46 is provided with an on/off switch 66, a set of keys 68 for selecting an applied voltage waveform, a knob 70 for selecting the voltage level of the waveform, another knob 72 for selecting the frequency of the waveform, a first LCD indicator 74 for displaying a value of actual voltage applied, and a second LCD indicator 76 for displaying a value of actual frequency applied. Timing panel 48 has an on-off switch 78, a keypad or keyboard 80 for setting the duration of stimulation of a selected treatment point, as well as an LCD indicator 82 of the actual length of a treatment. Housing 38 is additionally provided with a master power switch 84 for the entire functional or treatment unit 14.

Figure 3:
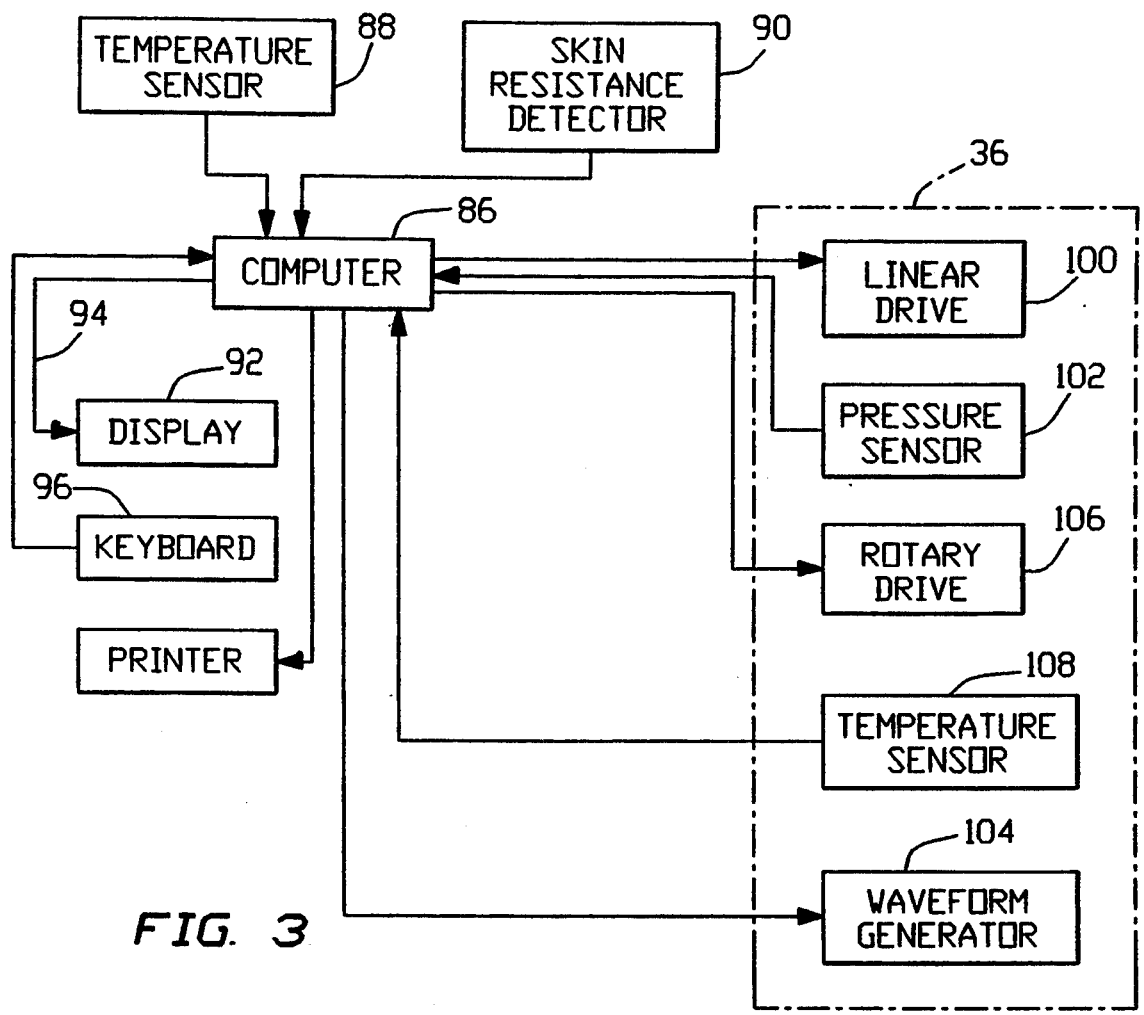
FIG. 3 is a block diagram of functional components of the apparatus of FIG. 1.

As illustrated in FIG. 3, functional or treatment unit 14 contains a computer 86 which receives electrical data-encoding signals transmitted to unit 14 from a temperature sensor 88 in probe 16 and an electrical resistance detector 90 in probe 22. Computer 86 also receives instructions from an operator via an alphanumeric keyboard 96. The instructions inform the computer as to the identity of a selected diagnostic point. In response to the signals from sensors 88 and 90 and keyboard 96, computer 86 determines a range of normal skin temperatures and skin resistances for the selected point and displays the normal ranges, as well as the actual measured parameters, on a display or video type monitor 92 (FIGS. 1 and 3). Monitor 92 is operatively connected to computer 86 via a lead or multiple 94 for displaying the results of a determination made by computer 86.

Computer 86 is also operatively connected to keypads 54, 64, 68, and 80, displays 52, 62, 74, 76, and 82, and knobs 70 and 72, for coordinating the operations thereof. Accordingly, in response to the measured skin temperature and resistance at a selected diagnostic point and possibly in response to the normal ranges displayed by computer 86 on monitor 92, an operator selects a treatment mode, a duration and an intensity of treatment of at least one treatment point on the patient's skin.

Usually, the treatment point is the same as the diagnostic point at which the temperature and resistance measurements were made via probes 16 and 22. However, it is possible that, in the course of treating a patient, a different treatment point is selected which corresponds to the same organs as the diagnostic point. It is even possible, depending on the course of treatment, that in a single treatment session, several points are treated with different modalities or combinations of modalities. For example, a treatment point on the ear may be subjected to heat, pressure and electrical energy, while another treatment point on the leg or foot corresponding to the same organ is subjected to thermal treatment only. The results of the treatment are determined when the patient returns for a subsequent treatment session. At the beginning of each treatment session, probes 16 and 22 are used to measure temperature and resistance at one or more diagnostic points. Computer 86 may be programmed to store the results of each diagnostic measurement and the following treatment, including the selected modalities, the treatment point, and the intenisty and duration of treatment. In the case of electrical treatment, the computer may memorize the selected/applied voltage, waveform and frequency. At the onset of a treatment session, the parameters of prior treatments, as well as the prior diagnostic measurements, may be recalled from storage by computer 86 in response to instructions entered via keyboard 96.

Upon selection of parameters of a pressure treatment, a thermal treatment, and/or an electrical treatment, via panels 42, 44, and/or 46 and the duration and intensity of the treatment via panel 48, computer 86 may display the selected parameters on monitor 92, together with the history of treatment of the particular patient. Of course, the treatment history of a patient is identified to computer via keyboard 96.

In the case that pressure alone is to be applied to a treatment point, the user or operator uses keypads 54 and 80 to set the intensity and duration of pressure treatment. Subsequently, the operator manipulates treatment probe 36 so that an operative tip 98 thereof is in superficial contact with the selected treatment point. Operative tip 98 has a diameter of 2 mm if it is being used for treating a diagnostic/treatment point on the ear. That tip is removed and replaced with a larger tip (3 mm) (not shown) when probe 36 is used for treating a point on a part of the body other than the ear.

As depicted in FIG. 3, probe 36 may be provided with a translatory or linear drive 100 which is responsive to signals from computer 86 to press tip 98 into the patient's skin with the force and the duration determined by instructions from the operator.

As further shown in FIG. 3, probe 36 is provided with a pressure or force sensor 102 which monitors the force applied to the patient via tip 98 and which transmits a feedback signal to computer 86. The feedback signal enables computer 86 to precisely control the pressure applied to the patient at the selected treatment point.

In an alternative mode of acupressure operation of unit 14, the operator manipulates treatment probe 36 to press tip 98 into the patient at the selected treatment point. The computer 86 monitors the applied pressure via sensor 102 and shows the value of the actual pressure via display 52. The operator monitors display 52 to check that the pressure applied is the specified pressure. As a safety feature, an alarm generator (not shown) may be provided in unit 14 for generating an alert signal upon determination that the selected pressure has been exceeded.

A similar procedure is followed in the event that the mode of treatment indicated by computer 86 via monitor or display 92 is a thermal treatment or an electrical treatment. In the latter case, the operator specifies the waveform (e.g., square, rectangular, sawtooth, sinusoidal) via keys 68 and sets the voltage and frequency of the waveform via knobs 70 and 72. Upon a subsequent juxtaposition of treatment probe tip 98 to the selected treatment point, computer 86 energizes a waveform generator 104 located in probe 36 (or, alternatively, in housing 38). The selected waveform is produced by generator 104 and transmitted over a patient's skin surface for a period of time and at a voltage and a frequency selected by an operator via keypad 80 and knobs 70 and 72.

Where a recommended mode of treatment determined by computer 86 is thermal, the operator so instructs computer 86 via the controls on panel 44. The operator selects the rate and the direction of rotation of tip 98 via keypad 64 and buttons 58 and 60. In addition, a level of pressure may be selected via keypad 54.

Upon a proper positioning of operative tip 98, the tip is turned by a rotary drive 106 under the control of computer 86. Rotary drive is preferably located in probe 36. The rate of rotation of probe tip 98 is monitored by computer 98 and its value is indicated by computer 86 via digital display 62. A temperature sensor 108 may be operatively connected to tip 98 for real-time monitoring of skin temperature during a thermal treatment. This measured temperature may be displayed on display 62 or monitor 92.

It is to be noted that computer 86 may be informed, for example, via keyboard 96, that probe 36 is in position for treatment to commence. Keyboard 96 is also used to inform computer 86 of the identities of diagnostic or treatment points. Accordingly, when obtaining a series of temperature and resistance measurements via probes 16 and 22, the operator identifies each successive diagnostic point to the computer prior to or immediately after a probe 16 or 22 is used. Similarly, if a procedure contemplates the treatment of several biologically active points, each point in the sequence is identified to computer 86.

Figure 4:
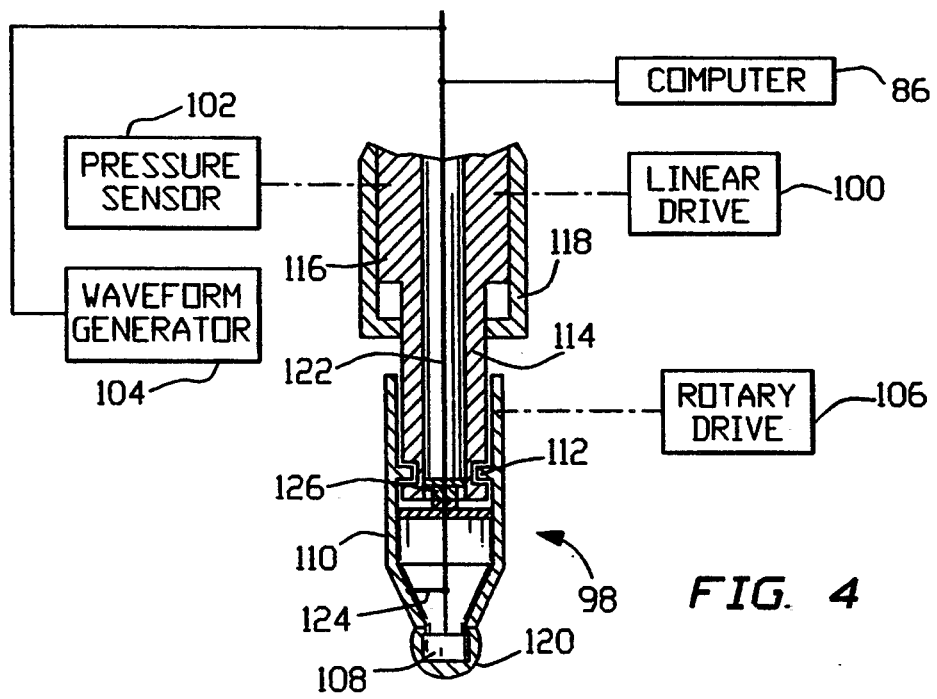
FIG. 4 is partially a schematic cross-sectional view and partially a block diagram of a treatment probe shown in FIGS. 1 and 3.

Tip 98 is a composite tip capable of performing acupressure, thermopuncture and electro-acupuncture treatments individually or in combination with one another. Tip 98 may take, for example, a form as illustrated in FIG. 4. Tip 98 includes a rotatable element 110 at a free end. Element 110 is rotatably mounted via an interdigitating annular groove and rib arrangement 112 to the distal end of a component 114 in turn slidably mounted via splines 116 to a frame 118. Rotatable element 110 is formed at an end opposite component 114 with a hollow ball 120 carrying temperature sensor 108. Sensor 108 is connected via a multiple line 122 to computer 86.

Rotatable element 110 is made of an electrically conductive material and also serves as an electrode for electro-acupuncture procedures. A lead 124 extends as part of multiple line 122 to waveform generator 104. A brush type assembly 126 is provided for enabling current and voltage transfer between sliding component 114 and rotating element 110.

It is to be noted that probe 36 may be held by a mechanical support such as an articulated armature with lockable joints (not illustrated). Such a support may be used to maintain the probe at a selected treatment point upon a manually positioning of the probe at the treatment point. Once computer 86 is informed, e.g., via keyboard 96, that probe 36 is in position, the computer transmits signals to drive 100, drive 106 and/or waveform generator 104, thereby automatically implementing the treatment determined by the operator using keypads 54, 56, 68, 80 and/or keyboard 96 in response to the temperature and skin resistance inputs from sensor 88 and detector 90 (FIG. 3).

As mentioned above, the diagnostic and treatment probes have replaceable operative tips, a 2 mm probe tip for diagnostic points on the ear and a 3 mm probe tip for other points. In addition, the provision of a single treatment probe with selectably applicable plural treatment modalities facilitates treatment procedures.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for use in treating a patient, comprising the steps of:
    measuring at least one predetermined physiological parameter at a predetermined point on the patient's skin, said parameter being taken from the group including temperature and electrical skin resistance;
    generating an electrical signal encoding the measured physiological parameter;
    transmitting said electrical signal to a computer;
    operating said computer to automatically determine a range of normal values of said physiological parameter at said predetermined point;
    displaying said range and a value of the measured physiological parameter on a display; and
    upon displaying said range and said value of the measured physiological parameter, treating a selected point on the patient's skin with at least one of a plurality of treatment modes including pressure treatment, heat treatment, and electrical treatment.

2. The method defined in claim 1 wherein said step of treating includes the steps of:
    providing a treatment probe having first means for applying heat to said selected point and second means for conducting electrical current to said selected point;
    manually placing said treatment probe at said selected point; and
    automatically operating said treatment probe to control intensity and duration of said mode of treatment at said selected point upon said step of placing.

3. The method defined in claim 1 wherein said step of treating includes the step of controlling intensity and duration of application of a selected treatment mode, further comprising the step of displaying parameter settings identifying the mode, intensity and duration of treatment.

4. The method defined in claim 1 wherein said selected point is different from said predetermined point.

5. The method defined in claim 1 wherein said selected point and said predetermined point are identical.

6. A method for use in treating a patient, comprising the steps of:

providing a treatment probe having a first operative tip, first means for applying heat to a predetermined point on a patient's skin surface via said operative tip and second means for conducting electrical current to said predetermined point via said operative tip, said operative tip having a first size;

manipulating said treatment probe to place said operative tip at said predetermined point;

operating at least one of said first means and said second means to apply a preselected treatment to said predetermined point via said operative tip;

automatically operating said treatment probe to control intensity and duration of said preselected treatment;

removing said operative tip from said treatment probe;

upon completion of said step of removing, attaching to said treatment probe a second operative tip having a second size different from said first size;

moving said treatment probe to position said second operative tip in contact with the patient's skin surface; and activating at least one of said first means and said second means to apply a pre-established treatment to the patient's skin surface via said second operative tip.

7. The method defined in claim 6, further comprising the step of instructing a computer as to said intensity and duration prior to said step of operating, said computer being connected to said treatment probe, said step of automatically operating including the step of operating said computer to control intensity and duration of treatment.

8. The method defined in claim 6 wherein said steps of operating include the step of applying both heat and electrical energy to said predetermined point and controlling the intensities and durations of application of heat and electrical current.

9. The method defined in claim 6, further comprising the step of displaying parameter settings identifying the mode, intensity and duration of treatment.

10. A device for use in treating a patient, comprising:
a handle;
an operative tip connected to said handle;
first treatment means operatively connected to said tip for applying a generally selectable amount of heat to a predetermined point on a patient's skin via said tip;
second treatment means operatively connected to said tip for applying a selectable amount of electrical energy to said predetermined point via said tip; and
third treatment means operatively connected to said tip for automatically controlling the degree of pressure applied to the patient's skin via said tip.

11. The device defined in claim 10 wherein said first treatment means includes:
first selection means for selecting an amount of heat to be applied to said predetermined point;
heating means operatively connected to said tip for elevating the temperature thereof to a magnitude in accordance with a selection made via said first selection means; and
first control means operatively connected to said first selection means and to said heating means for controlling the operation thereof in accordance with a selection made via said first selection means;
said second treatment means including:
second selection means for selecting an amount of electrical energy to be applied to said predetermined point;
electrical current generating means operatively connected to said tip for conducting through said tip an amount of current determined in accordance with a selection made via said second selection means; and
second control means operatively connected to said second selection means and to said current generating means for controlling the operation thereof in accordance with a selection made via said second first selection means.

12. The device defined in claim 11 wherein said first treatment means includes means for rotating said tip relative to said handle.

13. The device defined in claim 12, further comprising third selection means operatively connected to said first treatment means for selecting a rate of rotation of said tip relative to said handle.

14. The device defined in claim 11 wherein said first selection means and said second selection means include means for selecting a duration of application of energy to said predetermined point.

15. The device defined in claim 11 wherein said first control means and said second control means comprise computing means operatively connected to said first and said second selection means, said heating means and said current generating means for controlling duration and intensity of heat application via said heating means and electrical energy application via said current generating means.

16. The device defined in claim 15, further comprising a video monitor operatively connected to said computing means for displaying mode, duration and intensity of treatment.

17. The device defined in claim 10 wherein said first treatment means includes means for controlling intensity and duration of heat application.

18. The device defined in claim 10 wherein said second treatment means includes means for controlling intensity and duration of application of electrical energy.

19. The device defined in claim 10 wherein said second treatment means includes means for controlling voltage and frequency of an electrical signal applied to the patient's skin at said predetermined point.

20. A method for use in treating a patient, comprising the steps of:
measuring at least one predetermined physiological parameter at a predetermined point on the patient's skin, said parameter being taken from the group including temperature and electrical skin resistance;
generating an electrical signal encoding the measured physiological parameter;
in response to said step of generating, providing information to an operator as to the measured physiological parameter; and
in response to the information as to the measured physiological parameter, treating a selected point on the patient's skin with at least one of a plurality of treatment modes including pressure treatment, heat treatment, and electrical treatment.

21. The method defined in claim 20 wherein said step of providing information includes the step of operating a computer to automatically determine a range of normal values of said physiological parameter at said predetermined point.

22. The method defined in claim 21 wherein said step of providing information further includes the step of displaying information regarding the measured pyshiological parameter.

23. The method defined in claim 20 wherein said selected point is different from said predetermined point.

24. The method defined in claim 20 wherein said selected point and said predetermined point are identical.

25. A device for use in treating a patient, comprising:
a handle;
an operative tip connected to said handle;
first treatment means operatively connected to said tip for rotating said tip relative to said handle; and
second treatment means operatively connected to said tip for applying a selectable amount of electrical energy to said predetermined point via said tip.

26. The device defined in claim 25, further comprising selection means operatively connected to said first treatment means for selecting a rate of rotation of said tip relative to said handle.

27. The device defined in claim 25, further comprising selection means operatively connected to said first treatment means for selecting a direction of rotation of said tip relative to said handle.

28. A method for use in treating a patient, comprising the steps of:
providing a treatment probe having a rotatable operative tip and treatment means operatively connected to said operative tip for conducting electrical current to a predetermined point on a patient's skin surface via said operative tip;
manipulating said treatment probe to place said operative tip in contact with said predetermined point; and
rotating said operative tip in a predetermined direction while maintaining said operative tip in contact with said predetermined point.

29. The method defined in claim 28, further comprising the step of operating said treatment means to conduct electrical current to said predetermined point via said operative tip.

30. The method defined in claim 28, further comprising the step of automatically controlling the degree of pressure applied to the patient's skin via said operative tip.

31. The method defined in claim 28, further comprising the step of varying a rate of rotation of said operative tip.

32. The method defined in claim 28 wherein said operative tip is removably connected to said probe and has a first size, further comprising the steps of removing said operative tip from said treatment probe and, upon completion of said step of removing, attaching to said treatment probe a second operative tip having a second size different from said first size.

33. The method defined in claim 28, further comprising the step of displaying parameter settings identifying the mode, intensity and duration of treatment.

34. A method for use in treating a patient, comprising the steps of:
providing a treatment probe having first means for applying heat to a predetermined point on a patient's skin surface and second means for conducting electrical current to said predetermined point;
manually placing said treatment probe at said predetermined point;
operating at least one of said first means and said second means to apply a preselected treatment to said predetermined point; and
automatically controlling the degree of pressure applied to the patient's skin via said operative tip during said step of operating.

35. A method for use in treating a patient, comprising the steps of:
providing a treatment probe having first means for applying heat to a predetermined point on a patient's skin surface and second means for conducting electrical current to said predetermined point;
manually placing said treatment probe at said predetermined point;
operating at least one of said first means and said second means to apply a preselected treatment to said predetermined point;
instructing a computer as to said intensity and duration prior to said step of operating, said computer being connected to said treatment probe; and
automatically operating said computer to control intensity and duration of treatment in accordance with predetermined instructions fed to said computer during said step of instructing.

36. The method defined in claim 35, further comprising the step of operating said computer to automatically control the degree of pressure applied to the patient's skin via said treatment probe during the application of the preselected treatment to said predetermined point.

37. A device for use in treating a patient, comprising:
a handle;
an operative tip connected to said handle;
first treatment means operatively connected to said tip for applying a generally selectable amount of heat to a predetermined point on a patient's skin via said tip; and
second treatment means operatively connected to said tip for applying a selectable amount of electrical energy to said predetermined point via said tip; and
means operatively connected to said first treatment means and said second treatment means for preselecting a duration of application of energy to said predetermined point.

* * * * *